(12) United States Patent
Webster, Jr. et al.

(10) Patent No.: US 8,136,241 B2
(45) Date of Patent: Mar. 20, 2012

(54) METHOD FOR MAKING A LOW OHMIC PRESSURE-CONTACT ELECTRICAL CONNECTION BETWEEN THE RING ELECTRODE UNDER SURFACE AND THE LEAD WIRE

(75) Inventors: Wilton W. Webster, Jr., Altadena, CA (US); Mario Solis, Glendale, CA (US)

(73) Assignee: Biosense Webster, Inc., Diamond Bar, CA (US)

( * ) Notice: Subject to any disclaimer, the term of this patent is extended or adjusted under 35 U.S.C. 154(b) by 103 days.

(21) Appl. No.: 10/706,024

(22) Filed: Nov. 12, 2003

(65) Prior Publication Data

US 2005/0097737 A1 May 12, 2005

(51) Int. Cl.
*A61B 5/042* (2006.01)
*H01R 43/04* (2006.01)

(52) U.S. Cl. ......................................... 29/863; 607/122

(58) Field of Classification Search .................... 29/595, 29/857, 861–863, 508, 433, 455.1; 600/373, 600/374, 372, 377; 607/119, 122, 116; 439/867, 439/877
See application file for complete search history.

(56) References Cited

U.S. PATENT DOCUMENTS

| | | | | | |
|---|---|---|---|---|---|
| 2,286,097 | A | * | 6/1942 | Johnson | .......................... 29/863 |
| 3,717,839 | A | * | 2/1973 | Aldridge | ........................ 439/431 |
| 4,592,372 | A | * | 6/1986 | Beranek | ........................ 607/119 |
| 4,777,955 | A | * | 10/1988 | Brayton et al. | ............... 600/374 |
| 5,458,629 | A | | 10/1995 | Baudino et al. | |
| 5,855,552 | A | * | 1/1999 | Houser et al. | .................. 600/374 |
| 6,032,061 | A | * | 2/2000 | Koblish | ......................... 600/372 |
| 6,144,870 | A | * | 11/2000 | Griffin, III | ..................... 600/374 |
| 6,171,277 | B1 | | 1/2001 | Ponzi | |
| 6,324,415 | B1 | | 11/2001 | Spehr et al. | |
| 6,505,401 | B1 | | 1/2003 | Doan | |

FOREIGN PATENT DOCUMENTS

JP 57-191306 12/1982

OTHER PUBLICATIONS

Davies et al., The Rate Dependence of Confor Polyurethane Foams, Mar. 1, 1999, Cellular polymers, vol. 18, No. 2, 1999, pp. 117-136.*

* cited by examiner

*Primary Examiner* — Livius R Cazan
(74) *Attorney, Agent, or Firm* — Christie, Parker & Hale, LLP

(57) ABSTRACT

A method for attaching a ring electrode to the shaft of the tip section of a catheter comprises passing an electrode lead wire through a lumen in the catheter and out an exit hole in the tip section. The portion of the electrode lead wire extending out of the exit hole is stripped of non-conductive coating and wrapped around the shaft and secured in a clove hitch arrangement. The wrapped electrode lead wire is pulled tight while the material of the shaft is heated to embed the electrode lead wire in the shaft so that its outermost surface is generally flush with the surface of the shaft. The exit hole is sealed and a ring electrode, having a flared skirt is slipped over the shaft to a position over the wrapped electrode lead wire and exit hole. It is then swaged to reduce its outer diameter to about that of the outer diameter of the shaft of the tip section to thereby create a low ohmic connection with the electrode lead wire.

10 Claims, 4 Drawing Sheets

METHOD FOR MAKING A LOW OHMIC PRESSURE-CONTACT ELECTRICAL CONNECTION BETWEEN THE RING ELECTRODE UNDER SURFACE AND THE LEAD WIRE

FIELD OF THE INVENTION

This invention relates to electrophisiology catheters and, in particular, to an improved method for attaching ring electrodes to the tip section of an electrophisiology catheter shaft.

BACKGROUND OF THE INVENTION

Electrophisiology catheters have been in common use in medical practice for many years. They are used to map and stimulate electrical activity in the heart and to ablate sites of aberrant electrical activity. Among the various types of electrodes used in constructing electrophisiology catheters are ring electrodes. These are metal rings positioned at various intervals along the length of the tip section. The ring electrodes are electrically connected, via electrode lead wires which extend through a lumen in the catheter, to electrical instruments, e.g., a monitor, stimulator or source of energy, e.g., RF energy, for ablation.

A conventional method for making the electrical connection between an electrode lead wire and a ring electrode is to draw the electric lead wire out of a lumen in the tip section through an exit hole that extends from the lumen to the side surface of the shaft of the catheter tip. The distal end of the electrode lead wire, stripped of any non-conductive coating, is then welded or soldered onto the inner surface of a ring electrode. The ring electrode is then slipped over the tip shaft to a position directly over the exit hole while drawing the electrode lead wire back into the lumen. The ring electrode is then secured in place, e.g., by swaging or by the application of an appropriate adhesive. A resin, e.g., polyurethane resin, is often applied to the margins or edges of the ring electrode to assure a smooth transition between the outer circumferential surface of the ring electrode and the outer circumferential surface of the catheter shaft.

Conventional methods for mounting ring electrodes on a catheter have certain drawbacks. For example, because the electrode lead wire must be drawn back into the lumen of the catheter tip section as the ring is slipped over the shaft of the tip section, the exit hole cannot be sealed and visually inspected before the ring electrode is swaged or glued over the exit hole. Further, the ring electrode must have a sufficiently larger diameter than that of the shaft of the catheter tip to slide over the shaft to its final position. Stretching the shaft of the tip section to reduce its diameter is one technique that allows the use of a closer fitting ring electrode. This technique, however, is operator dependent and tends to lead to inconsistent quality in the placement of the ring electrode on the shaft. Further, ring electrodes mounted by the conventional method tend to "pull away" from the shaft of the tip section, i.e., the edge of the ring electrode tends to separate from the surface of the catheter tip shaft along the outside of the curve, during tight bending of the tip section.

For these and other reasons, there is a need to find a method for attaching ring electrodes to the shaft of the catheter tip section that is less costly, more efficient and does not exhibit the above mentioned drawbacks and disadvantages of the conventional method.

SUMMARY OF THE INVENTION

The present invention provides a method for attaching a ring electrode to the shaft of a catheter tip section. The method comprises first providing a catheter tip section comprising at least one lumen extending therethrough. The catheter tip section has an exit hole extending from the outer surface of the shaft to the lumen for each ring electrode to be mounted on the tip shaft. Electrode lead wires, which have a non-conductive coating pass into the lumen of the tip section, with the distal end of one electrode lead wire being drawn out of each exit hole. The portion of the electrode lead wire that extends out of the exit hole is stripped of its non-conductive coating and wrapped around the shaft of the catheter tip section, preferably at least one full turn, and more preferably, at least two full turns. In a particularly preferred embodiment, the electrode lead wire which extends from the exit hole is wrapped twice around the shaft of the catheter tip section and looped under the first turn in a clove hitch arrangement. Other arrangements that secure the electrode lead wire to the surface of the shaft of the tip section may be used as desired.

In a preferred embodiment, the electrode lead wire is wrapped sufficiently tightly so that it embeds into the outer surface of the catheter tip shaft so that the outermost surface of the electrode lead wires is generally flush with the outer surface of the catheter tip shaft. Preferably, the portion of the catheter tip section adjacent the exit hole is heated to a temperature sufficient to soften the material of the tip shaft, e.g., to about 90° C. to 110° C. for polyurethane, to facilitate embedding of the electrode lead wire in the catheter tip shaft. The exit hole is then sealed with suitable sealant and a ring electrode having an inner diameter slightly greater than the outer diameter of the shaft of the tip section is slid over the shaft to a position directly above the wrapped electrode lead wires and exit hole. The ring electrode has a flared skirt at its proximal end to facilitate slippage of the ring electrode over the shaft of the catheter tip section. A particularly preferred ring electrode has a skirt that, beginning at about the midpoint of the ring electrode, flares radially outwardly at an angle of from about 4° to about 8° and more preferably at an angle of about 6° on each side. Once the ring electrode is positioned over the wrapped electrode lead wire and exit hole, it is swaged to reduce its inner and outer diameters so that it is tightly secured to the tip shaft and makes sufficient pressure contact with the underlying electrode lead wire to provide a low ohmic connection. To prevent movement of the ring electrode before swaging, a small amount of fast drying cure adhesive may be applied over the exit hole and/or electrode lead wires before the ring electrode is moved into its final position.

BRIEF DESCRIPTION OF THE DRAWINGS

These and other features and advantages of the present invention will be better understood by reference to the following detailed description when considered in conjunction with the accompanying drawings wherein:

FIG. 1b is a side cross-sectional view of the catheter tip section of FIG. 1a.

DETAILED DESCRIPTION OF THE INVENTION

In accordance with the present invention, there is provided an improved method for attaching a ring electrode to a catheter shaft for making a low ohmic connection to an electrode lead wire. The method is applicable to catheters of any size and only requires that the body to which the ring electrode is attached has a generally circular cross-section and at least one lumen therethrough for passage of an electrode lead wire.

The method comprises first providing a distal tip section of a catheter having at least one lumen extending longitudinally through at least a portion of the tip section. The tip section may be the distal portion of an integral, elongated catheter body or may be a separate structure that is attached to the distal end of the catheter body as is well known in the art. See, for example, U.S. Pat. No. 6,171,277, which is incorporated herein by reference. The catheter body and tip section may be made of any material suitable for use in the construction of electrophisiology catheters. Polyurethane is an example of a suitable material.

Figure 1A:
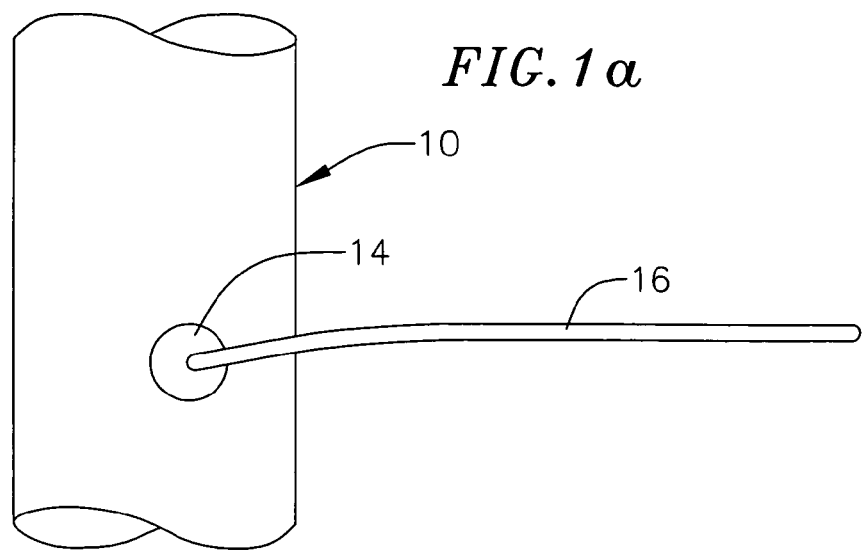
FIG. 1a is a side view of a portion of a catheter tip section showing an exit hole and an electrode lead wire extending out of the exit hole.
Figure 1B:
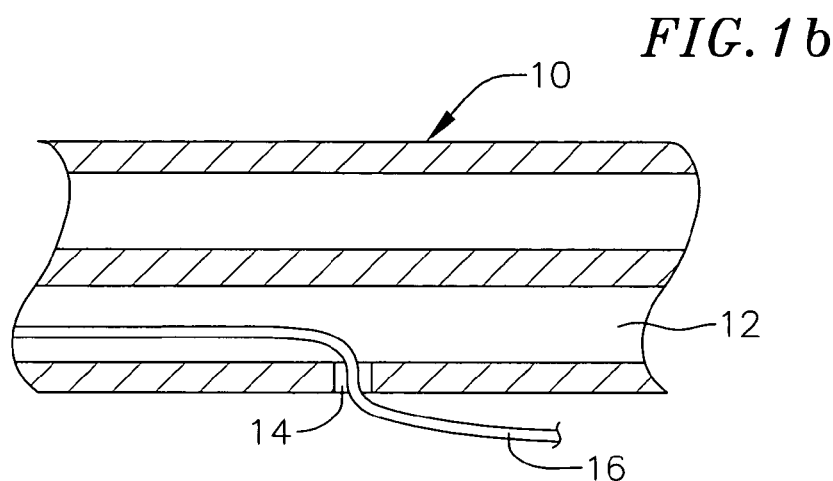

With reference to FIGS. 1a and 1b, the shaft of the tip section 10 comprises a lumen 12 and a small exit hole 14 that extends between the lumen 12 and the outer side surface of the shaft. The size of the exit hole is not critical and can be formed, for example, by inserting a needle through the wall of the shaft and heating the needle sufficiently to form a permanent hole. Such an exit hole is sufficiently large to enable an electrode wire to be pulled through the hole, e.g., by a microhook or the like, and yet sufficiently small to be easily sealed.

An electrode lead wire 16 is pulled through the lumen 12 of the tip section 10 and out of the exit hole 14. The length of the electrode lead wire 16 that extends out of the exit hole 14 is not critical, but is sufficient to allow the electrode lead wire 16 to be wrapped around the shaft of the tip section 10 the desired number of turns. The electrode lead wire 16 may be made of any suitable, preferably non-oxidizing, material and may have any suitable diameter. A preferred electrode lead wire is 0.003 inch MONEL® 400 wire (high tensile strength nickel-copper alloy), which is coated with a nonconductive coating.

Figure 2:
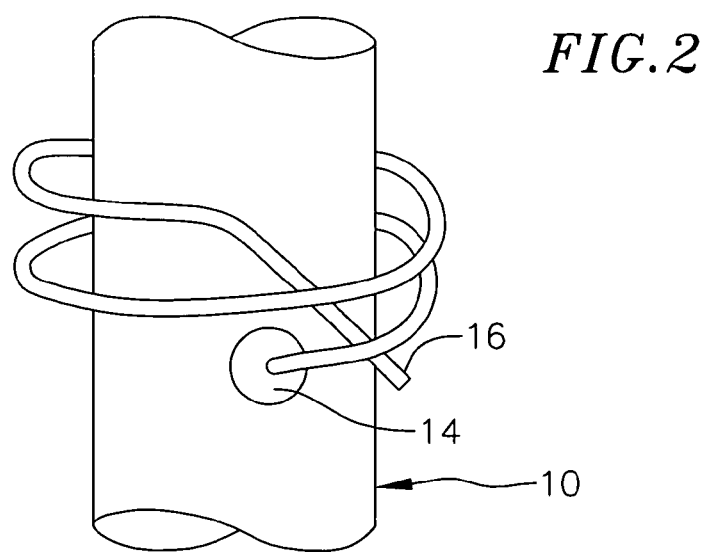
FIG. 2 is a side view of a portion of a catheter tip section showing an exit hole and an electrode lead wire extending out of the exit hole and wrapped around the tip shaft in a clove hitch arrangement.
Figure 3:
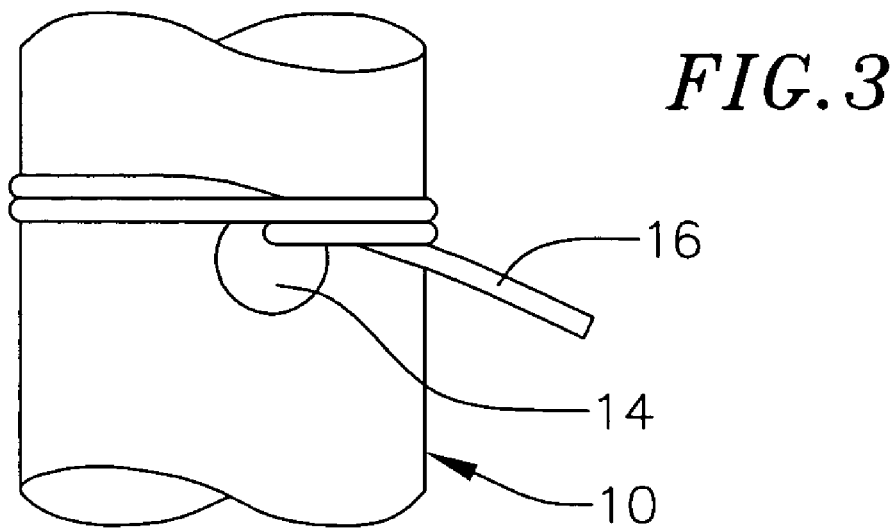
FIG. 3 is a side view showing the clove hitch arrangement of FIG. 2 that has been tightened around the shaft.

The portion of the electrode lead wire 16 that extends out of the exit hole 14 is stripped of insulation and wrapped around the shaft of the catheter tip 10. A particularly preferred wrapping technique is shown in FIGS. 2 and 3. In this technique, the electrode lead wire 16 extending from the exit hole 14 is wrapped around the shaft of the catheter tip 10 in one direction for two full turns, with the two turns proceeding in a distal direction. The free end of the electrode lead wire 16 is passed under the two wraps in a clove hitch arrangement, as shown. After wrapping, the free end of the electrode lead wire 16 is pulled to eliminate any slack in the wraps. The local area of the shaft adjacent to the exit hole is heated, preferably to a temperature sufficient to soften the material of the tip section 10. For polyurethane, a temperature of from about 90° C. to about 110° C. is presently preferred. Once the tip section 10 is heated, the electrode lead wire 16 is further pulled to tighten the wires against the outer surface of the catheter tip section 10 to embed the wire 16 into the side surface of the tip shaft. Finally, the end of the electrode lead wire is trimmed adjacent to the electrode lead wire wrap.

Figure 4:
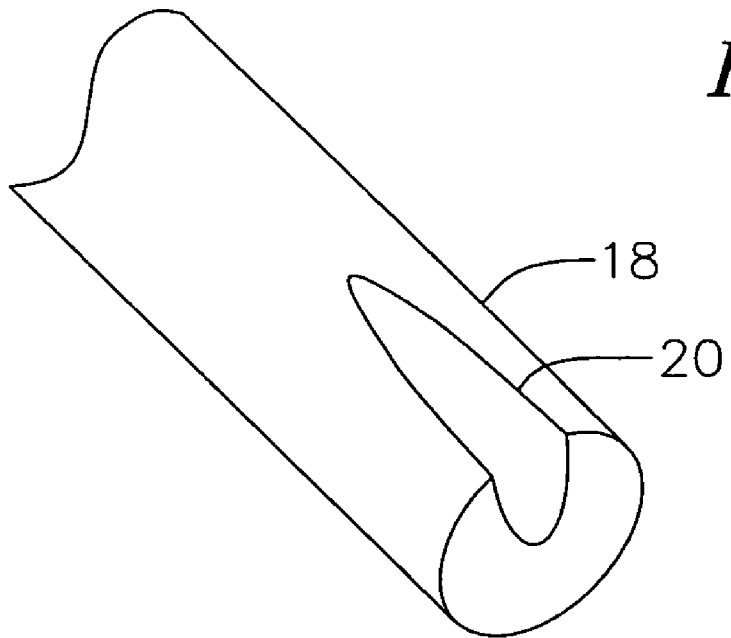
FIG. 4 is a perspective view of a preferred heating cradle.

It is understood that, while heating to facilitate embedding of the wire wraps is preferred, it is not necessary to practice the invention. Moreover, when heating is used, any temperature that softens the plastic material of the shaft of the tip section may be employed. Further, any technique or device that allows heating, particularly localized heating, may be used. With reference to FIG. 4, a preferred heating device consists of a heating block or rod 18 that has been configured to form a cradle 20 to receive the portion of the tip section adjacent the exit hole 14. The heating block or rod 18 can be heated by any conventional method, e.g., it may be heated by or comprise an electric heating element.

To prevent contamination of the interior of the catheter, the exit hole is sealed after the wire wrap is formed. Any suitable non-toxic sealant can be used. Polyurethane resin is presently preferred. The present method allows visual inspection of the seal before the ring electrode 22 is positioned over the exit hole.

Figure 5:
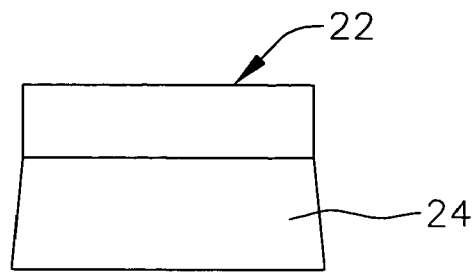
FIG. 5 is a side view of a ring electrode having a flared skirt.
Figure 6:
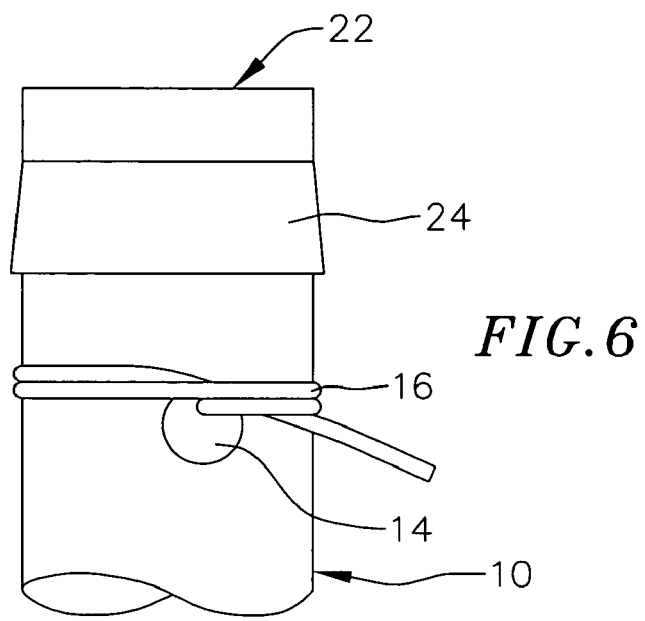
FIG. 6 is a side view of a portion of a catheter tip section showing a flared ring electrode being slipped over the shaft toward the wrapped electrode lead wire.

With reference to FIG. 5, a ring electrode 22 is provided which has an inner diameter slightly greater than the outer diameter of the tip shaft to allow it to be slipped over the shaft of the catheter tip 10 to a location over the wrapped electrode lead wire 16 and exit hole 14. For example, if the tip section 10 has an outer diameter of 0.084 inch, a ring electrode having an inner diameter of 0.085 inch is preferred. The ring electrode may be made of any suitable conductive, preferably non-oxidizing, material. One preferred material is platinum iridium alloy.

The ring electrode 22 has flared skirt 24, which tapers outwardly, preferably over about one-half of the ring width on the proximal side. The flared skirt 24 tapers outwardly and proximally preferably at an angle of from about 4° to about 8° and more preferably at an angle of about 6°. A ring electrode 22 having a flared skirt 24 is preferred for several reasons. First, it makes installation of the ring electrode 22 onto the tip section shaft easier. That is, the flare aids insertion of the tip into the ring and acts as a ledge to push on while sliding the ring onto the catheter tip. In constructions involving the assembly of multiple ring electrodes, the ring edge of the flared skirt 24 can fit easily over the wire wraps without displacing them. The flare allows the operator to consistently position the wire wrap under the center of the ring electrode 22 by pushing the ring over the wrap until it encounters the non-flared portion of the ring 22.

An angle of about 4° to about 8° and particularly about 6° is preferred as it is sufficiently flared to allow the ring electrode to slip over the catheter shaft and over one or more electrode wire wraps located distally of the position where the ring electrode is to be secured. Such an angle is generally not too great to cause cracking in the ring electrode during formation of the flared skirt and reforming to a cylinder during swaging.

The flared skirt 24 can be created in any suitable manner. A preferred technique is to press one end of a conventional ring electrode 22 (without a flared skirt) over a tool that has the desired flare angle with sufficient force to cause the wall of the ring electrode 22 to expand radially outwardly to match the angle of the tool.

Just before the ring electrode is placed over the wrapped electrode lead wire 16 and the exit hole 14, it is preferred to place a drop of fast drying glue over the exit hole and adjacent wire wrap to temporarily hold the ring electrode 22 in place and prevent movement of the ring electrode 22 prior to the subsequent swaging process. Cyanoacrylate, which cures by pressure contact, is a preferred fast drying glue.

Figure 7:
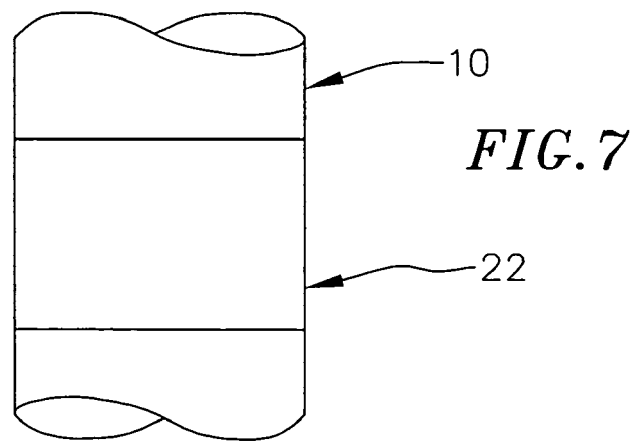
FIG. 7 is a side view of a portion of a catheter tip section showing a ring electrode positioned over the wrapped electrode lead wire after swaging.
Figure 8:
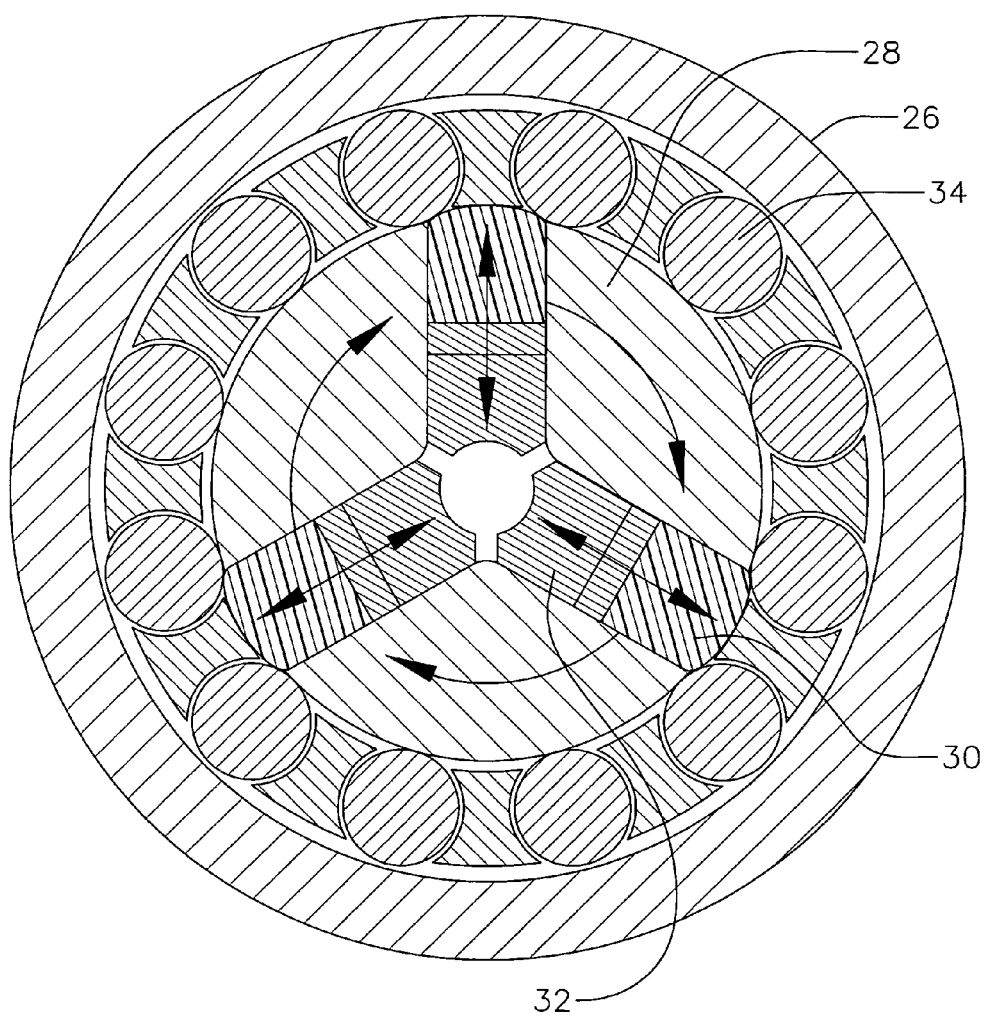
FIG. 8 is a schematic cross-sectional view of a rotary swager showing generally its operation.

Once the ring electrode 22 has been positioned directly over the wrapped electrode as shown in FIG. 7, lead wire 16 and exit hole 14, it is swaged to reduce its diameter by means of a rotary swaging tool, e.g., a Fenn Amca International Model AF rotary swager. FIG. 8 shows in general how rotary swaging works. In the figure, head 26 is fixed. A motorized spindle 28 comprises slots for holding backers 30 and dies 32. The spindle passes the backers 30 over rollers 34 which causes the backers 30 to impact the dies 32 as the spindle 28 rotates. In this arrangement, the backers 30 deliver a blow to the dies 32 which in turn impact the ring electrode 22 that is positioned within the dies 32 of the rotary swager. When a backer 30 is between two roller positions, centrifugal forces cause it to move radially outwardly making it possible for the associated die 32 to open while the dies 32 are rotating around the ring electrode. The operation continues until the outer diameter of the ring electrode is reduced to about the outer diameter of the shaft of the tip section.

The dies 32, which have a length of about 0.75 inch and are flared or tapered over the proximal half of the dies forming a cone-shaped entrance into the space within the dies. The distal half of the dies forms a generally cylindrical space having a diameter about equal to the outer diameter to which the ring electrode are swaged, i.e., the outer diameter of the shaft of the tip section. The cone-shaped entrance enables the diameter of the ring electrode to be reduced slowly, thus minimizing the risk of cracking or other damage to the ring electrode. It has been found that an angle of from about 2° to about 4° and particularly about 3° on each side is suitable for this purpose.

The preceding description has been presented with references to presently preferred embodiments of the invention. Persons skilled in the art and technology to which this invention pertains will appreciate that alterations and changes in the described structures can be practiced without meaningfully departing from the principle, spirit and scope of this invention. Accordingly, the foregoing description should not be read as pertaining only to the precise structures described and shown in the accompanying drawings, but rather should be read as consistent with and as support for the following claims, which are to have their fullest and fairest scope.

What is claimed is:

1. A method for attaching a ring electrode to a catheter comprising:
    providing a catheter tip section comprising a tubular shaft having at least one lumen extending therethrough and at least one exit hole extending from the outer surface of the shaft of the catheter tip section to the at least one lumen;
    passing a portion of an electrode lead wire through the at least one lumen and out of the exit hole;
    wrapping the portion of the electrode lead wire that extends out of the exit hole around the circumference of the shaft of the catheter tip section at least one full turn;
    sliding a ring electrode over the shaft of the catheter tip section and positioning the ring electrode directly over the circumferentially wrapped electrode lead wire, wherein the ring electrode is pre-fabricated to have a first portion that is generally non-flared and a second portion that is generally flared, and wherein positioning the ring electrode over the wrapped electrode lead wire comprises pushing the second portion of the ring electrode over the wrapped electrode lead wire until the wrapped electrode lead wire encounters the first portion of the ring electrode, thereby positioning the wrapped electrode lead wire under the ring electrode at a position generally between the first and second portions of the ring electrode;
    swaging the ring electrode to reduce its outer diameter sufficiently to secure the ring electrode to the shaft of the catheter tip, wherein the outer diameter of the swaged ring electrode is about the same as the outer diameter of the shaft of the catheter tip.

2. The method as claimed in claim 1, wherein the electrode lead wire is wrapped around the circumference of the shaft of the catheter tip section sufficiently tightly so that the outermost surface of the electrode lead wire is generally flush with the outer surface of the shaft of the catheter tip section.

3. The method as claimed in claim 1, wherein the electrode lead wire is wrapped circumferentially around the shaft of the tip section at least two turns.

4. The method as claimed in claim 1, wherein the electrode lead wire is wrapped circumferentially around the shaft of the tip section and secured thereto in a clove hitch arrangement.

5. The method as claimed in claim 1, wherein the second portion of the ring electrode is flared radially outwardly at an angle of about 4 to about 8 degrees.

6. The method as claimed in claim 5, wherein the second portion of the ring electrode is flared radially outwardly at an angle of about 6 degrees.

7. The method as claimed in claim 1, wherein the electrode lead wire comprises a non-conductive coating and the non-conductive coating is removed from the portion of the electrode lead wire that extends out of the exit hole.

8. The method as claimed in claim 1, wherein the shaft of the tip section is made of polyurethane and is heated to from about 90° C. to about 110° C. during the wrapping step.

9. The method as claimed in claim 1, further comprising sealing the exit hole with a sealant, and wherein the sliding the ring electrode over the shaft of the catheter tip section occurs after the sealing the exit hole.

10. The method as claimed in claim 9, wherein the sealant comprises a polyurethane resin.

\* \* \* \* \*